United States Patent
Carlsson et al.

(10) Patent No.: US 6,491,520 B1
(45) Date of Patent: Dec. 10, 2002

(54) DENTAL INSTRUMENT

(75) Inventors: Lennart Carlsson, Gothenburg (SE); Rolf Bornstein, Stockholm (SE); Dan Ericson, Malmo (SE)

(73) Assignee: MediTeam Dental AB, Savedalen (SE)

( * ) Notice: Subject to any disclaimer, the term of this patent is extended or adjusted under 35 U.S.C. 154(b) by 0 days.

(21) Appl. No.: 09/763,574

(22) PCT Filed: Apr. 23, 2001

(86) PCT No.: PCT/SE99/01459

§ 371 (c)(1),
(2), (4) Date: Apr. 23, 2001

(87) PCT Pub. No.: WO00/12022

PCT Pub. Date: Mar. 9, 2000

(30) Foreign Application Priority Data

Aug. 27, 1998 (SE) .............................. 9802868

(51) Int. Cl.⁷ ................................. A61C 3/03
(52) U.S. Cl. ........................................ 433/118
(58) Field of Search ................. 433/118, 143, 433/165, 166

(56) References Cited

U.S. PATENT DOCUMENTS

| | | | |
|---|---|---|---|
| RE11,118 E | * 10/1890 | Browne | 433/165 |
| 1,813,741 A | * 7/1931 | Harper | 433/165 |
| 2,656,559 A | * 10/1953 | Wiseman | 433/166 |
| 4,283,174 A | 8/1981 | Sertich | |
| 4,753,594 A | 6/1988 | Croll | |
| 4,895,515 A | * 1/1990 | Axelson | 433/166 |
| 5,261,818 A | * 11/1993 | Shaw | 433/166 |
| 5,504,961 A | * 4/1996 | Yang | 433/118 |
| 5,653,591 A | 8/1997 | Logé | |
| 5,689,159 A | * 11/1997 | Culp et al. | 433/143 |
| 5,971,758 A | * 10/1999 | Hugo et al. | 433/118 |

FOREIGN PATENT DOCUMENTS

| | | |
|---|---|---|
| EP | 0398893 B1 | 11/1988 |
| WO | WO 98/20838 | 5/1998 |
| WO | WO 98/29053 | 7/1998 |
| WO | WO 98/41164 | 9/1998 |
| WO | WO 99/34765 | 7/1999 |

* cited by examiner

*Primary Examiner*—Todd E. Manahan
(74) *Attorney, Agent, or Firm*—Connolly Bove Lodge & Hutz LLP

(57) ABSTRACT

A dental instrument is provided for removing caries attacked dentine in connection with chemical-mechanical treatment of caries by means of a caries-dissolving solution applied to the caries for loosening the caries tooth substance. The instrument comprises a tool head with a number of scraping edges or bristles for scraping away the loosened caries tooth substance. In the spacings formed therebetween drops of the gel solution used for the chemical-mechanical treatment can be carried (transported) up to the tooth treatment site. The instrument is power-driven in order to provide the tool head with a predetermined scraping motion.

24 Claims, 3 Drawing Sheets

DENTAL INSTRUMENT

Figure 1:
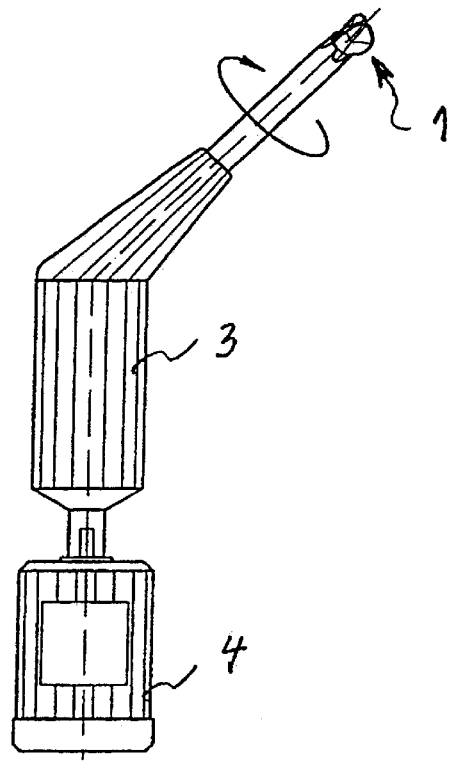

The present invention relates to a dental instrument for removing caries attacked dentine.

In traditional caries treatment the attacked tooth substance is removed mechanically by means of a dentist's drill or a cutting excavator. Such a caries treatment is often a painful and unpleasant experience for the patient. Some of the patients feel so uncomfortable with the treatment that they wait far too long before they visit a dentist, which means that it is often too late to save the caries attacked teeth. Extraction of the teeth is then the only treatment method that is left.

However, there are other methods which are based on a chemical-mechanical treatment for the removal of the caries attacked substance. Such methods are described in SE 460258, SE 507437 and SE 98.00025-0. According to these methods a preparation in the form of a two-component liquid is mixed and then immediately applied to the caries lesion. Functioning in a biological way, the liquid makes the caries attacked substance soft without causing any damage to the tooth or the soft tissue. After 10–15 seconds the dentist can start removing the carious substance by means of a scraping instrument. The scraping continues until all caries substance has been removed. Then the cavity is filled with a suitable filling material.

According to SE 460258 the two-component liquid consists of a sodium hypochlorite component and a nitrogen-containing. component. The nitrogen-containing component consists in this case of three nitrogen-containing compounds with different charge states in its side chain; one neutral, one with a negative net charge and one with a positive net charge.

Unlike conventional mechanical caries treatment methods the biological treatment method is usually not painful at all. Neither does it require any investments in expensive equipments. It only requires a scraping instrument to remove softened carious dentine material.

Traditional excavator instruments, however, are not suitable for this purpose as they are cutting and not made for just scraping away already softened dentine material from different types of cavities and therefore could damage healthy dentine.

An instrument specifically made for removing softened carious dentine is previously disclosed in SE 96.04626-3. This instrument makes it possible to manually scrape in different directions and the scraping edges of the tool head of the instrument are adapted to all types of caries lesions. The instrument comprises a star-shaped tool head having four symmetrically arranged scraping edges with a curved, preferably spherical, outer contour (periphery) for scraping away softened carious substance.

The instrument can also be used to pick up drops of the liquid solution used for the chemical-mechanical treatment method and apply these drops to the caries lesion. This is possible because of the open, empty spaces which are formed between the scraping edges of the tool head of the instrument and this function of the instrument is facilitated as the liquid solution which is used has a viscous, gel form.

So by using this type of scraping instrument which then also functions as a simple applicator for the gel used for the treatment, there is no need for the dentist to invest money in any expensive equipments for distribution and application of the liquid gel solution.

However, in cases where a relatively large amount of liquid is required for the treatment, it might be time-consuming to use any of said instruments as applicators as the instrument cannot pick up and carry so much volume of the liquid that would have been desired.

In SE 9700960-9 it is described a scraping instrument in which the tool head member has drop catching means in order to improve the ability to catch and carry liquid drops. The drop catching means can be made in the form of collars, flanges, surface enlargement portions, protrusions, grooves, holes, channels or the like.

Both of these instruments are made for manually scraping softened, carious dentine, ie. the scraping motion is made by hand.

As the scraping motion should be carried out in different directions and repeated until all carious dentine has been removed, it might be a hard work for the dentist from an ergonomically point of view to fulfil the caries treatment. The dentist has to position the instrument as well as control the instrument with respect to the scraping direction. At the same time the scraping motion should not affect any of the healthy teeth. It should not be allowed to apply too heavy pressure from the instrument on the tooth.

It is an object of this invention to provide a scraping instrument which facilitates for the dentist to remove carious dentine. Specifically, it is an object to unload the specific scraping motion from the dentist so that he can concentrate on positioning the instrument. This means a more efficient treatment procedure.

A further object of this invention is to speed up the scraping operation so that each caries treatment procedure is shortened.

Also a further object of the invention is to provide a scraping instrument with a more controlled scraping motion and a more steady scraping speed, which means that the scraping motion is independent of different users of the instrument, which in turn means a more predictable result from the treatment procedure.

According to the invention the scraping instrument is power-driven, i.e. the instrument is equipped with, or connected to, for instance an electric motor for driving the tool head of the instrument according to a predetermined motion pattern. For instance it could be a rotating, low-speed motion, a reciprocating motion, a pendulating, wobbling or oscillating motion.

According to a preferred embodiment the instrument has a star-shaped tool head and a shaft for connecting the instrument to a rotating machine (power tool).

Also other tool heads could be used, such as brush type tool heads. According to a further preferred embodiment a set of different instruments, i.e. instruments with different tool heads but easy connectable to the rotating machine, could be used.

Figure 2:
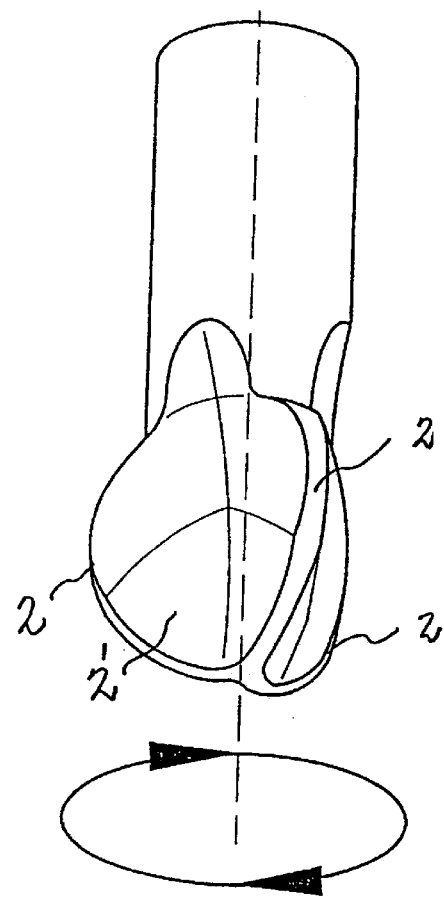
Figure 3:
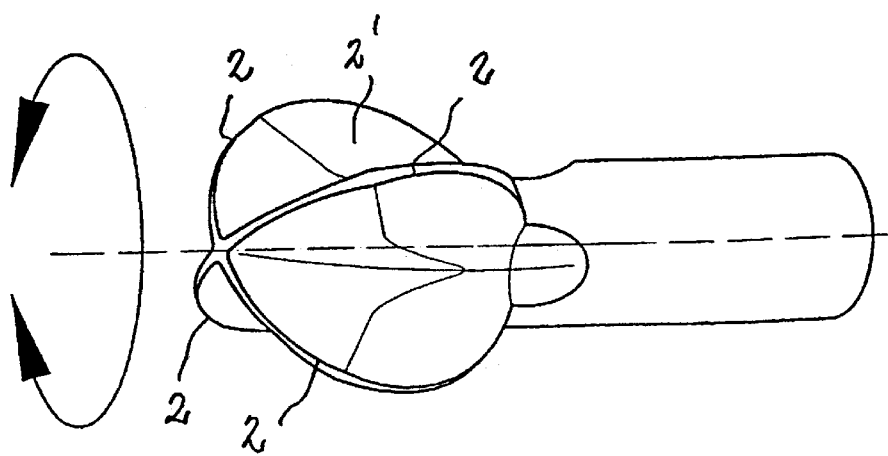
Figure 4:
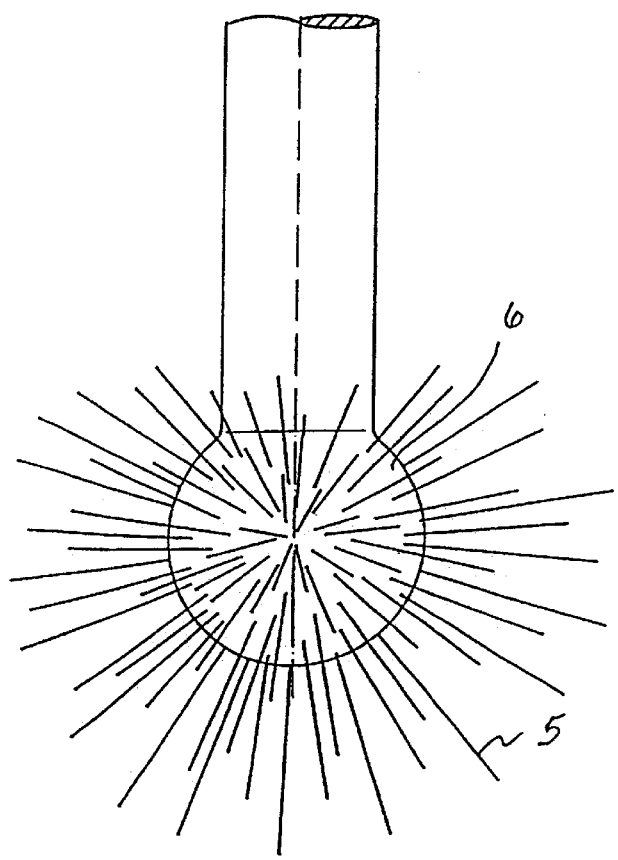
Figure 5:
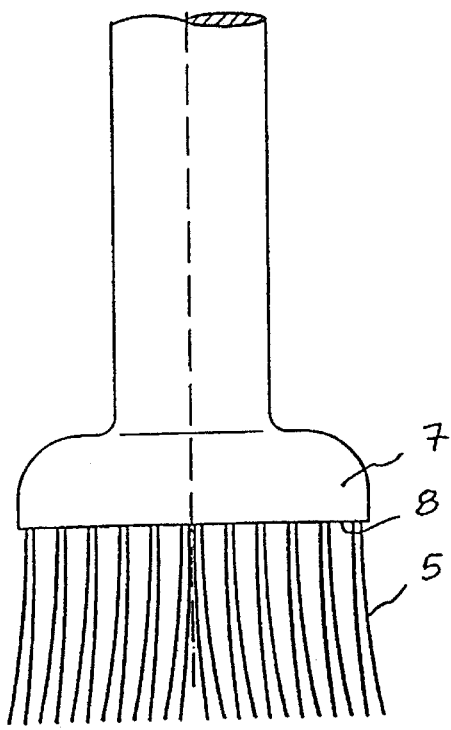
Figure 6:
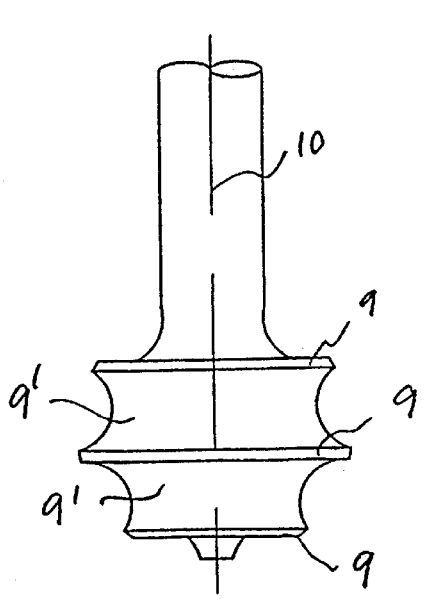
Figure 7:
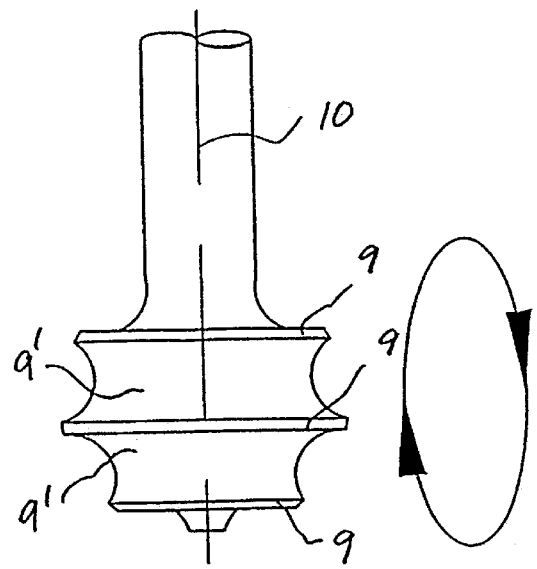
Figure 8:
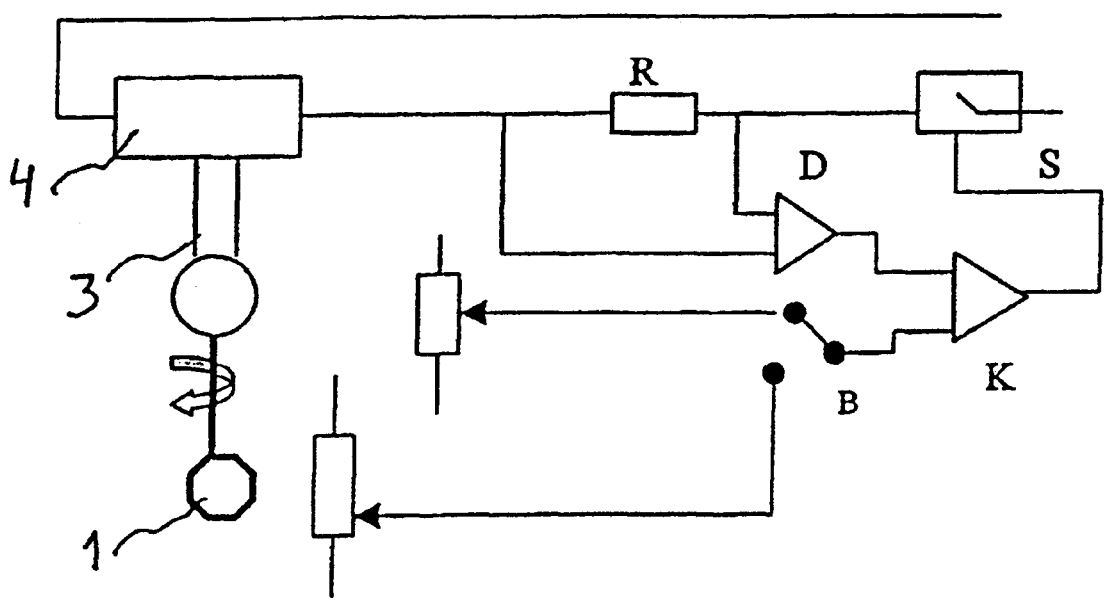

In the following some examples of instruments according to the invention will be described more in detail with reference to the accompanying drawings, wherein FIG. 1 is an overall view of an instrument, FIG. 2 illustrates a star-shaped tool head with scraping edges more in detail, FIG. 3 illustrates a star-shaped tool head with four scraping edges, FIG. 4 illustrates a tool-head in the form of a "brush", FIG. 5 illustrates a further embodiment of a brush-type tool head, FIG. 6 and 7 illustrate a tool head having a geometry adapted to an axial oscillating motion and an elliptical motion, respectively, and FIG. 8 illustrates schematically a torque controller for the instrument.

As illustrated in FIG. 1 the instrument comprises a tool head 1 having a spherical outer contour. The tool head is intended to be used for scraping a tooth cavity after a biochemical caries treatment. The tool head has in this case a star-shaped geometry formed by three symmetrically arranged scraping edges 2 having a circular periphery. The scraping edges 2 are extending radially outwards in three different directions and thanks to the circular periphery both the bottom and the sides of the cavity can be scraped with one and the same star-shaped tool head.

The tool head itself could have the same form as in the instrument illustrated in SE 9604626-3, but in which the scraping motions are carried out completely by hand. Similar to the previously known instrument, of course also this instrument could have more or less than three symmetrically arranged scraping edges. In FIG. 3 it is illustrated as an example a tool head having four scraping edges 2. However, a common feature for these embodiments is the form of the scraping edges 2: a substantially circular or curved periphery to permit scraping of the bottom as well as the sides of a tooth cavity.

In contrast to the previously known hand instrument, in which two tool members are arranged with a hand grip member therebetween for handling the instrument entirely by hand, the instrument according to the present invention has a bent connecting part (shaft) 3 to a driving tool or similar rotating machine 4, preferably an electric driving motor. In this way a rotary motion, preferably a reversible motion, is applied to the tool head. However, this motion should not be compared with the motion of the high speed dentist's drill.

According to the chemical-mechanical treatment method it is the softened caries tooth substance that should be removed by the instrument. The rotary speed for the tool head is then approximately 10–1000 rpm, which should be compared with 20.000–40.000 rpm for a conventional dentist's drill, and even 200.000–600.000 rpm for a conventional high speed turbine for dental use.

In case an ordinary driving motor for a dentist's drill is used as a driving tool in our application, then the motor speed must be reduced to approximately 10–1000 rpm, which also could be arranged by means of a speed reduction gear or adaptor connected to the output of the driving motor.

As the scraping instrument concurrently should be used as an uncomplicated applicator for the caries dissolving liquid gel, ie the instrument should be able to carry drops of the liquid to the caries lesion, then it is important that the dentist can control the rotary speed from zero and upwards in a simple way. Unintentional high rotary speeds could otherwise easily throw off the gel drops from the tool head and cause unnecessary spillage.

The driving motor could be connected to the electric power supply or for practical reasons having rechargeable batteries.

In FIG. 4 it is illustrated a tool head in the form of a brush 5 made of a metallic, polymer or other similar fibre material. The bristles could be directed either in the axial or in the radial direction or in all directions (a spherical brush) from a substantially spherical main body 6. By means of the brush structure the transformation of the gel liquid in the caries lesion interface is accelerated. By making the bristles more stiff some mechanical abrasion could be achieved.

In FIG. 5 it is illustrated a further embodiment of a brush-formed tool head. In this case the bristles 5 are directed in the axial direction from a main body 7 with a substantially planar end surface 8.

In FIGS. 6 and 7 it is illustrated a tool head having a geometrical shape adapted for another type of motion, in this case an axially oscillating motion (FIG. 6) or a motion having an elliptical pattern (FIG. 7). The scraping edges 9 have a circular symmetrical contour in a plane perpendicular to the longitudinal axis 10 of the tool head, ie in contrast to the previously in FIGS. 2 and 3 described tool heads with substantially longitudinally arranged scraping edges 2.

In the illustrated example there are three such parallell scraping edges 9 with the central one having the larger radius. By means of the rounded spacings 9' between the scraping edges, also in this case drops of the liquid gel, which is used for the chemical-mechanical caries treatment method, can be more easily picked up and carried by the instrument.

In the previous examples the tool head makes either a "single" rotary motion or a more complicated motion pattern such as a reciprocating motion, oscillating motion, wobbling motion, elliptic motion or the like, which is indicated in the figures.

A reciprocating motion can be achieved by means of an angle gear which transforms the rotary motion of the motor axis to a reciprocating motion on the tool head 1. Such gears are known per se and will therefore not be described in any detail here. A similar arrangement is used for an angle piece in connection with endodontic teeth treatment methods in which an axial or rotating oscillating motion is used. The oscillating motion could also be provided by means of the motor operating voltage. Compare electrical adjusting means for numerically controlled machines. Further alternatives for providing the driving motion to the tool head is to use for instance linear motors or so-called voice-coil technique which is used today in loud-speakers and in computer disc memories to position the reading head.

In Swedish patent application 96.04626-3 it is mentioned that one of the objects of the scraping instrument design is to scrape away the loosened caries, but as far as possible without affecting healthy dentine. This should be the same also for a machine instrument and this can be achieved, like in the hand instruments, by designing the cutting angles in such a way that the risk for cutting in to healthy dentine is reduced.

In the hand-held scraping instruments the cutting angles are then made less cutting, ie the cutting angles are less acute, in order to prevent any abrasion of healthy dentine material. However, healthy dentine might be damaged even with an instrument like the one described in said patent 96.04626-3 if too much pressure is applied on the scraping motion.

In the same way a machine instrument might damage healthy dentine if too much pressure is applied against the surface when the tool head is rotating or moved in any of the pattern that has been described above. It is therefore an object to limit this possibility. This can be achieved by providing the machine with means for sensing the pressure against the instrument directly or indirectly by measuring the torque for rotating the instrument. By measuring the torque continuously and comparing it with a set limit value determined experimentally for a specific tool head geometry the machine can be alarmed or stopped as soon as this value has been reached so that the risk for damaging healthy tooth dentine is reduced.

The surface of a caries lesion can be more or less hard, see for instance Swedish patent application 98.03057-0. Therefore a relatively high torque for the instrument is sometimes required. However, the instrument must be handled very gently when working close to the tooth pulp to avoid any risks to go through the dentine separating the caries from the pulp. In such a case a lower torque limit is choosen which reduces the possibility for the instrument to cut into healthy dentine but which also forces the dentist to work more gently.

In one example of an instrument torque control the torque is measured by measuring the input current to the electric motor driving the tool. As soon as the current exceeds a predetermined value the machine is shut-off. In order not to manually have to reset and restart the machine again after a stop, and once the pressure on the tool head has been reduced, the motor current could be limited to a value corresponding to the actual torque. Another practical solution is to limit the motor current to a much less value when the torque limit has been reached. Then the machine starts rotating again as soon as the instrument has been unloaded. When the motor is rotating again this can easily be detected by measuring the electromotive force of the motor. As soon as the rotational speed has been returned the machine also returns to its predetermined value with the higher motor current and corresponding higher torque.

FIG. 8 shows by means of a block diagram how such a torque control could be accomplished. An electrical driving motor 4 is connected to the tool head 1 by means of a connector shaft. The motor current can be easily measured as the voltage over a resistor R in series with the driving motor 4. This signal is submitted to a comparator K via a differential amplifier D for comparing the signal from the differential amplifier D with a reference value or transformed to a digital signal for a computer chip controlling the machine. When the signal from the differential amplifier D exceeds the reference voltage then the status of the output signal is changed to an electronic control circuit S, to limit the motor current or shut-off the motor current as soon as the predetermined limit value has been reached. By means of a switch B a plurality of preset torque values could be selected.

The invention is not limited to the examples which have been illustrated here but can be varied within the scope of the accompanying claims. For instance the invention could also include a set of different instruments in which the tool heads are different but the connecting shafts the same so that each of them can be connected to one and the same driving tool.

What is claimed is:

1. Caries attacked dentine removing instrument used in chemical-mechanical treatment of caries by means of a caries-dissolving solution applied to the caries lesion for loosening the caries tooth substance, said instrument comprising a tool head (1) with a number of scraping, edges or bristles (2,5,9) for scraping away, on the caries lesion site, the loosened caries tooth substances and spacings (2',9') therebetween for carrying drops of the solution used for the chemical-mechanical treatment to the caries lesion, and power-driving means for providing the tool head (1) a predetermined scraping motion; the power-driven motion being adapted for scraping away the softened caries tooth substance, reducing the possibility of cutting into healthy dentine and carrying drops of the caries-dissolving solution without said substance or drops being thrown away and causing unnecessary spillage, and wherein the tool head is driven by an electric motor providing the tool head (1) with a rotary motion having a speed less than 1000 r.p.m. or wherein the tool head is driven by a reciprocating (oscillating) motion of approximately 10–1000 oscillations per minute.

2. Instrument according to claim 1 characterized in that the tool head (1) is provided with a rotary motion having a speed less than 1000 r.p.m.

3. Instrument according to claim 2 characterized in that the rotary motion is adjustable and reversible in the interval of 0–1000 r.p.m.

4. Instrument according to claim 1 characterized in that the tool head (1) is driven by a reciprocating (oscillating) motion wherein the oscillating motion is approximately 10–1000 oscillations per minute.

5. Instrument according to claim 1 characterized in that the tool head (1) has a substantially spherical outer contour.

6. Instrument according to claim 5 characterized in that the tool head (1) is star-shaped with a number of symmetrically arranged, curved scraping edges (2).

7. Instrument according to claim 5 characterized in that the tool head (1) is formed as a brush with a number of bristles (5) extending in the axial, radial or in all directions and wherein the bristles are made of a metal, a polymer or some other fibre material.

8. Instrument according to claim 5 characterized in that the tool head is made with a number of circular symmetrical scraping edges (9) with an oscillating motion.

9. Instrument according to claim 1 characterized in that it comprises means (R,D,K,S,B) for measuring the torque required for rotating the instrument.

10. Instrument according to claim 9 characterized in that the torque is measured continuously and compared with a predetermined limit value experimentally determined for a specific tool geometry.

11. Instrument according to claim 10 characterized by electronic control circuitry (S) to limit or shut-off the motor current when the limit value has been reached.

12. Instrument according to claim 11 characterized in that the torque is controlled by measuring the current supplied to the electric driving motor for the instrument.

13. A method of removing caries attacked dentine by chemical-mechanical treatment of caries by applying a caries-dissolving solution to the caries lesion for loosening the caries tooth substance and scraping away the loosened caries tooth substance employing the caries attacked dentine removing instrument of claim 1.

14. The method of claim 13 which comprises rotating the tool head (1) a speed less than 1000 r.p.m.

15. The method of claim 14 wherein the rotating is adjustable and reversible in the interval of 0–1000 r.p.m.

16. The method of claim 13 which comprises driving the tool head (1) by a reciprocating (oscillating) motion, wherein the oscillating motion is approximately 10–1000 oscillations per minute.

17. The method of claim 13 wherein the tool head (1) has a substantially spherical outer contour.

18. The method of claim 17 wherein the tool head (1) is star-shaped with a number of symmetrically arranged, curved scraping edges (2).

19. The method of claim 17 wherein the tool head (1) is formed as a brush with a number of bristles (5) extending in the axial, radial or in all directions and wherein the bristles are made of a metal, a polymer or some other fibre material.

20. The method of claim 17 wherein the tool head is made with a number of circular symmetrical scraping edges (9) with an oscillating motion.

21. The method of claim 13 which further comprises measuring the torque required for rotating the instrument.

22. The method of claim 21 which comprises measuring the torque continuously and comparing it with a predetermined limit value experimentally determined for a specific tool geometry.

23. The method of claim 22 which further comprises limiting or shutting off the motor current when the limit value has been reached using electronic control circuitry (S).

24. The method of claim 23 which further comprises controlling the torque by measuring the current supplied to the electric driving motor for the instrument.

* * * * *